US008425601B2

(12) United States Patent
Bruneau et al.

(10) Patent No.: US 8,425,601 B2
(45) Date of Patent: Apr. 23, 2013

(54) SPINAL STABILIZATION DEVICES AND METHODS OF USE

(75) Inventors: Aurelien Bruneau, Memphis, TN (US); Thomas A. Carls, Memphis, TN (US); Eric C. Lange, Collierville, TN (US); John Durward Pond, Jr., Germantown, TN (US); Kent M. Anderson, Memphis, TN (US); Henry Keith Bonin, Jr., Memphis, TN (US); Jonathan M. Dewey, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1323 days.

(21) Appl. No.: 11/530,662

(22) Filed: Sep. 11, 2006

(65) Prior Publication Data

US 2008/0065079 A1    Mar. 13, 2008

(51) Int. Cl.
*A61F 2/44* (2006.01)
*A61B 17/70* (2006.01)

(52) U.S. Cl.
USPC .................. 623/17.11; 606/256; 606/257

(58) Field of Classification Search .............. 606/246, 606/250, 252–257, 305; 623/17.11–17.16
See application file for complete search history.

(56) References Cited

U.S. PATENT DOCUMENTS

| | | | |
|---|---|---|---|
| 4,697,582 A | 10/1987 | William | |
| 5,011,497 A | 4/1991 | Persson et al. | |
| 5,180,393 A | 1/1993 | Commarmond | |
| 5,375,823 A | 12/1994 | Navas | |
| 5,415,661 A | 5/1995 | Holmes | |
| 5,423,816 A | 6/1995 | Lin | |
| 5,540,688 A | 7/1996 | Navas | |
| 5,672,172 A | 9/1997 | Zupkas | |
| 5,672,175 A * | 9/1997 | Martin | 606/86 A |
| 6,241,730 B1 | 6/2001 | Alby | |
| 6,248,106 B1 * | 6/2001 | Ferree | 606/263 |
| 6,267,764 B1 | 7/2001 | Elberg | |
| 6,402,750 B1 | 6/2002 | Atkinson et al. | |
| 6,554,831 B1 | 4/2003 | Rivard et al. | |
| 6,986,771 B2 | 1/2006 | Paul et al. | |
| 6,989,011 B2 | 1/2006 | Paul et al. | |
| 7,137,985 B2 | 11/2006 | Jahng | |
| 7,326,210 B2 * | 2/2008 | Jahng et al. | 606/86 A |
| 2003/0153914 A1 * | 8/2003 | Oribe et al. | 606/61 |
| 2003/0220642 A1 | 11/2003 | Freudiger | |
| 2003/0220643 A1 * | 11/2003 | Ferree | 606/61 |
| 2004/0002708 A1 | 1/2004 | Ritland | |

(Continued)

FOREIGN PATENT DOCUMENTS

| | | |
|---|---|---|
| EP | 0 669 109 A1 | 8/1995 |
| EP | 0 677 277 A2 | 10/1995 |

(Continued)

*Primary Examiner* — Kevin T Truong
*Assistant Examiner* — Matthew Lawson

(57) ABSTRACT

The present application is directed to methods and devices that provide for asymmetrical movement of vertebral members. In one embodiment, first and second anchors connect the rod to the vertebral members. The rod may be fixedly connected to the first anchor, and movably connected to the second anchor. A limiting device may be positioned on one or both sides of the second anchor. The limiting device or devices control an extent of movement between the rod and the second anchor during vertebral motion. In one embodiment, the device controls an amount of flexion and extension of the vertebral members.

22 Claims, 14 Drawing Sheets

U.S. PATENT DOCUMENTS

| | | | |
|---|---|---|---|
| 2004/0049189 A1 | 3/2004 | Le Couedic et al. | |
| 2004/0049190 A1* | 3/2004 | Biedermann et al. | 606/61 |
| 2004/0138662 A1* | 7/2004 | Landry et al. | 606/61 |
| 2004/0143264 A1 | 7/2004 | McAfee | |
| 2004/0147928 A1 | 7/2004 | Landry et al. | |
| 2004/0215191 A1* | 10/2004 | Kitchen | 606/61 |
| 2004/0236327 A1* | 11/2004 | Paul et al. | 606/61 |
| 2004/0236329 A1 | 11/2004 | Panjabi | |
| 2004/0267260 A1* | 12/2004 | Mack et al. | 606/61 |
| 2005/0065515 A1 | 3/2005 | Jahng | |
| 2005/0065516 A1* | 3/2005 | Jahng | 606/61 |
| 2005/0124991 A1 | 6/2005 | Jahng | |
| 2005/0149020 A1 | 7/2005 | Jahng | |
| 2005/0171540 A1* | 8/2005 | Lim et al. | 606/61 |
| 2005/0171543 A1 | 8/2005 | Timm et al. | |
| 2005/0177156 A1 | 8/2005 | Timm et al. | |
| 2005/0177157 A1 | 8/2005 | Jahng | |
| 2005/0203513 A1 | 9/2005 | Jahng et al. | |
| 2005/0203514 A1 | 9/2005 | Jahng et al. | |
| 2005/0203517 A1 | 9/2005 | Jahng et al. | |
| 2005/0203519 A1 | 9/2005 | Harms et al. | |
| 2005/0209698 A1 | 9/2005 | Gordon et al. | |
| 2005/0240265 A1* | 10/2005 | Kuiper et al. | 623/17.11 |
| 2005/0267470 A1* | 12/2005 | McBride | 606/61 |
| 2005/0288672 A1* | 12/2005 | Ferree | 606/61 |
| 2006/0106381 A1* | 5/2006 | Ferree et al. | 606/61 |
| 2006/0195093 A1 | 8/2006 | Jahng | |
| 2007/0055247 A1 | 3/2007 | Jahng | |
| 2007/0173822 A1* | 7/2007 | Bruneau et al. | 606/61 |
| 2007/0233085 A1* | 10/2007 | Biedermann et al. | 606/61 |
| 2008/0033435 A1* | 2/2008 | Studer et al. | 606/61 |
| 2008/0183212 A1* | 7/2008 | Veldman et al. | 606/254 |
| 2008/0183213 A1* | 7/2008 | Veldman et al. | 606/257 |
| 2008/0195159 A1* | 8/2008 | Kloss et al. | 606/305 |

FOREIGN PATENT DOCUMENTS

| | | |
|---|---|---|
| FR | 2 694 182 A1 | 2/1994 |
| WO | WO 02/07622 A1 | 1/2002 |
| WO | WO 03/047442 A1 | 6/2003 |
| WO | WO 2005/030029 A2 | 9/2004 |
| WO | WO 2005/030031 A2 | 9/2004 |

* cited by examiner

SPINAL STABILIZATION DEVICES AND METHODS OF USE

BACKGROUND

The present application is directed to spinal stabilization devices and methods and, more specifically, to devices and methods that provide for asymmetrical vertebral motion in first and second directions.

The spine is divided into four regions comprising the cervical, thoracic, lumbar, and sacrococcygeal regions. The cervical region includes the top seven vertebral members identified as C1-C7. The thoracic region includes the next twelve vertebral members identified as T1-T12. The lumbar region includes five vertebral members L1-L5. The sacrococcygeal region includes nine fused vertebral members that form the sacrum and the coccyx.

The vertebral members provide for movement in various directions. The movement may include flexion, extension, lateral bending, axial rotation, or a coupled combination of these movements. In a normal spine, more motion occurs in a first direction than in a second direction. By way of example, the vertebral members may provide for greater flexion than extension.

Various conditions may lead to damage of the vertebral members and/or intervertebral discs. The damage may result from a variety of causes including a specific event such as trauma, a degenerative condition, a tumor, or infection. Damage to the intervertebral discs and vertebral members can lead to pain, neurological deficit, and/or loss of motion. Vertebral rods may be implanted to redistribute stresses and/or restore proper alignment of the vertebral members. The rods extend along a section of the spine and may include a curved configuration to conform to the curvature of the spine. The rods may provide for motion of the vertebral members.

SUMMARY

The present application is directed to methods and devices that provide for asymmetrical motion of the vertebral members. In one embodiment, first and second anchors connect the rod to the vertebral members. The rod may be fixedly connected to the first anchor, and movably connected to the second anchor. A limiting device may be positioned on one or both sides of the second anchor. The limiting device controls an extent of movement between the rod and the second anchor during vertebral motion in first and second directions. In one embodiment, the device controls an amount of flexion and extension of the vertebral members.

DETAILED DESCRIPTION

The present application discloses devices and methods for supporting vertebral members. The support provides for asymmetrical movement of the vertebral members with a first amount of movement in a first direction, and a second lesser amount of movement in a second direction.

Figure 1A:
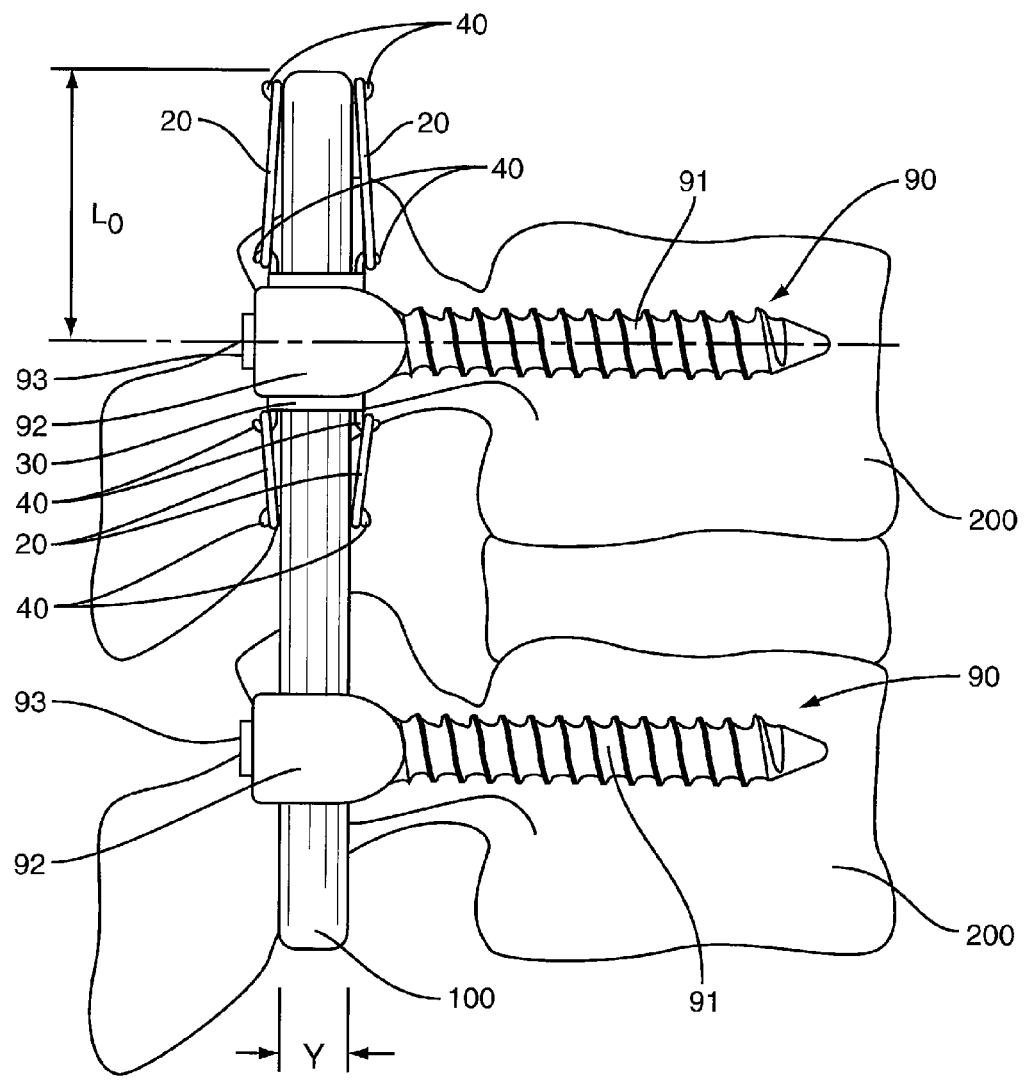
FIG. 1A-1C are side views illustrating a device according to one embodiment.

FIG. 1A illustrates one embodiment of a device for asymmetrical movement. The device includes a plurality of anchors 90 attached to vertebral members 200. A rod 100 is mated to the anchors 90 to support the vertebral members 200. In one embodiment, the rod 100 is constructed of a flexible material that bends during movement of the vertebral members 200. Rod 100 is fixedly positioned within the inferior anchor 90, and slidably engaged within the superior anchor 90 to slide relative to that anchor 90 during vertebral movement. Elastic members 20 connected to the rod 100 control the amount of sliding and therefore the amount of vertebral movement in the various directions.

Rod 100 may include an elongated shape and extend along a length of the vertebral members 200. In the embodiment of FIG. 1A, rod 100 extends along two adjacent vertebral members 200. Rod 100 may also include a longer length to extend along more than two vertebral members 200. In one embodiment, rod 100 may bend during movement of the vertebral members 200. The entire rod 100 may be constructed of a material that provides for bending, or one or more discreet sections of the rod 100 are constructed to be bendable either by their material construction or inclusion of a mechanical element. Rod 100 may further include a variety of different cross-sectional shapes and sizes, such as a circular cross-sectional shape. Rod 100 may include a substantially constant or variable diameter Y.

Anchors 90 attach the rod 100 to the vertebral members 200. In the embodiment of FIG. 1, each anchor 90 includes a shaft 91 with a saddle 92 positioned at one end. The shaft 91 may be threaded for insertion into and attachment with the vertebral member 200. Saddle 92 may include a pair of arms that are spaced apart a distance to receive the rod 100. In one embodiment, the arms form a substantially U-shaped space to position the rod 100. The saddle 92 may be rigidly connected to the shaft 91, or may be pivotally connected to the shaft 91. A fastener 93 attaches to the saddle 92 to maintain the rod 100 between the arms. In one embodiment, the fastener 93 includes threads that engage with threads on an upper edge of the saddle 92.

In one embodiment, the rod 100 is positioned along a posterior section of the vertebral members 200. In one embodiment of posterior positioning, rod 100 supports movement of the vertebral members 200 during flexion and extension. Rod 100 may also be positioned at other locations along the vertebral members 200 such as along a lateral or anterior section.

Figure 2:
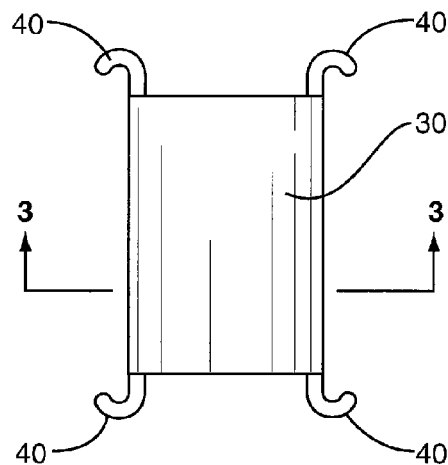
FIG. 2 is a side view illustrating a sleeve according to one embodiment.
Figure 3:
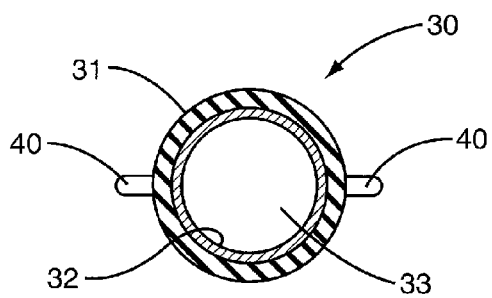
FIG. 3 is a cross section view along line 3-3 of FIG. 2 illustrating the sleeve according to one embodiment.

A sleeve 30 may be positioned within the saddle 92 and contain the rod 100. In the embodiment of FIG. 1A, sleeve 30 fits between the arms of the saddle 92. FIGS. 2 and 3 illustrated one embodiment of the sleeve 30. Sleeve 30 includes a cylindrical shape including an opening 33 with an inner diameter that is greater than the outer diameter Y of the rod 100. This provides for relative motion between the rod 100 and sleeve 30 during movement of the vertebral members 200. In one embodiment, sleeve 30 includes a length greater than the saddle 92. Sleeve 30 may include an outer surface 31 that contacts the saddle 92 and an inner surface 32 that contacts the rod 100. In other embodiments, sleeve 30 may be constructed from a single material. Sleeve 30 may be constructed of a plurality of materials. Examples of materials for the inner surface 32 include polyetheretherketone, titanium, polyeurathane, stainless steel, cobalt chrome, and polyethylene.

One or more elastic members 20 extend between the sleeve 30 and the rod 100. The elastic members 20 apply a force on the rod 100 during movement of the vertebral members 200 to control the extent of relative movement between the rod 100 and anchor 90. In one embodiment, the elastic members 20 are constructed of a resilient material that stretches and contracts during vertebral movement. Examples of the material may include surgical latex, chloroprene, MIT's "biorubber" (glycerol and sebacic acid), silicone, polyethylene, polyester, polyurethane, urethane, and polypropylene. When more than one elastic member 20 is used, the members 20 may have the same construction, or may include different constructions. Further, the elastic members 20 may each have the same material characteristics, such as shape, size, length, and elasticity, or each may include different characteristics. In one embodiment, the elastic members 20 form continuous bands.

Figure 4:
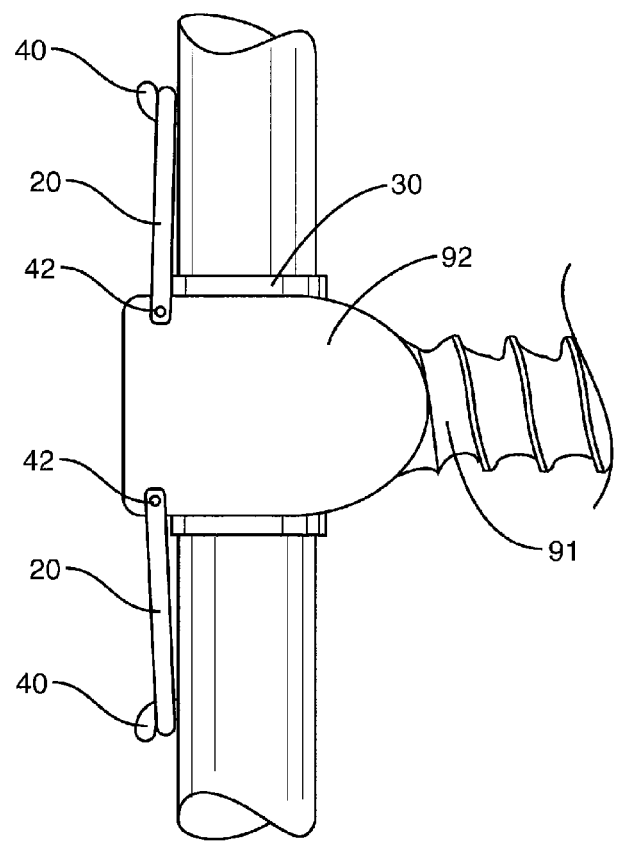
FIG. 4 is a side view illustrating elastic members attached to an anchor according to one embodiment.

The embodiment illustrated in FIG. 1A includes four elastic members 20 that extend between the sleeve 30 and the rod 100. In this embodiment, two members 20 are positioned on each of the opposing sides of the rod 100 (i.e., two elastic members 20 on each of the anterior and posterior sides, or medial and lateral sides). In other embodiments, different numbers of members 20 may be connected to the rod 100. FIG. 4 includes two elastic members 20 attached to the posterior side of the rod 100. In one embodiment, a single elastic member 20 is connected with the rod 100.

In one embodiment, elastic members 20 are positioned on the inferior and superior sides of the anchor 90. FIG. 1A illustrates one embodiment with elastic members 20 positioned on both sides. In other embodiments, elastic members 20 may be positioned on one of the inferior and superior sides.

Figure 5:
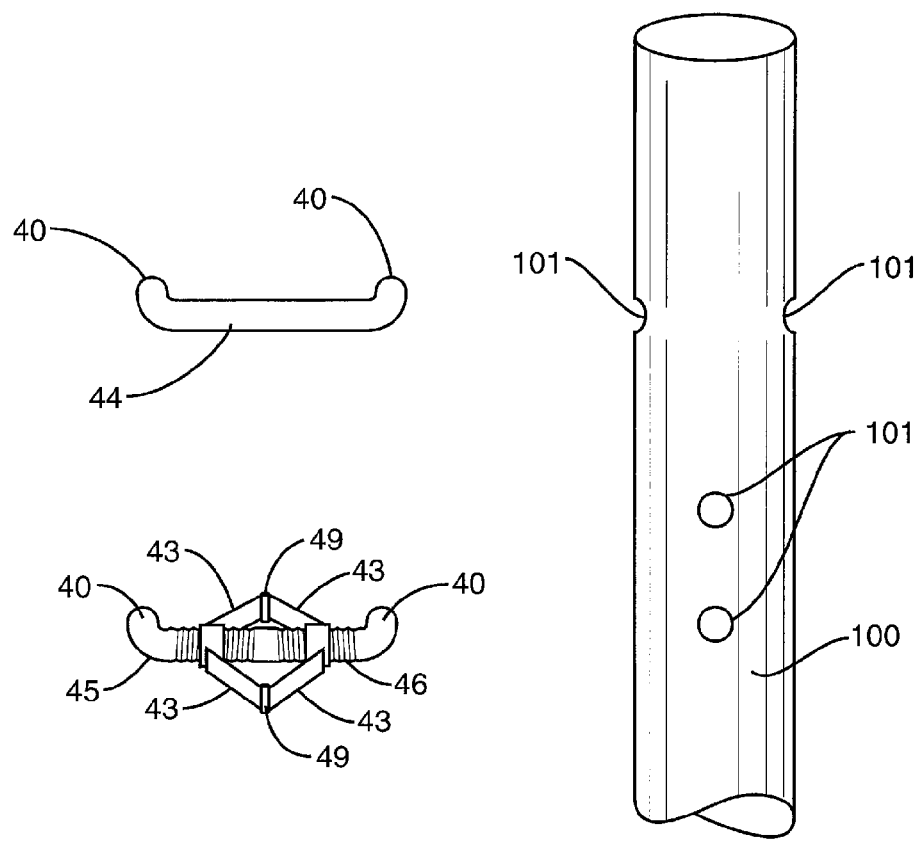
FIG. 5 is an exploded side view illustrating a rod and a pair of attachment arms according to different embodiments.

The elastic members 20 may connect with the rod 100, sleeve 30, and anchor 90 in a variety of manners. In one embodiment, arms 40 are positioned to receive the members 20. FIG. 1A illustrates one embodiment with arms 40 positioned on the rod 100 and the sleeve 30 to receive the members 20. Arms 40 may be attached to the elements in various manners including adhesives, soldering, brazing, welding, and fasteners. In one embodiment as illustrated in FIG. 5, rod 100 includes apertures 101 sized to receive the arms 40. Apertures 101 may extend completely through the rod 100, or a partial distance. Further, apertures 101 may be positioned at a variety of angular orientations. In one embodiment, arms 40 are part of a member 44 that is sized to fit within an aperture 101 with the arms 40 extending outward from the rod 100. In one embodiment, member 44 is held within the aperture 101 by adhesive, soldering, brazing, or fastener. Member 44 may also include threads that engage corresponding threads within the aperture 101.

Arms 40 may further be part of a member 45 that includes linkages 43 to maintain attachment with the rod 100. In the embodiment illustrated in FIG. 5, member 45 includes linkages 43 that are connected by a pivot 49. Rotation of the body 46 causes the linkages 43 to move away from and towards the body 46 to control an overall width. In a first state, the linkages 43 are positioned near the body 46 and the overall width of the member 45 is reduced to fit within the aperture 101. Once inserted, the body 46 is rotated causing the linkages 43 to expand outward and become wedged into the aperture 101 and firmly position the arms 40 to extend outward. Both of members 44, 45 include two arms 40, although other embodiments may include a single arm 40 sized to extend from the rod 100.

Figure 6:
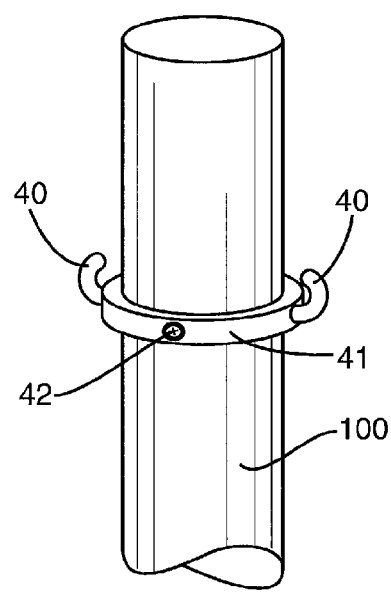
FIG. 6 is a side view illustrating a ring attached to a rod according to one embodiment.

FIG. 6 illustrates another embodiment with the arms 40 attached to a ring 41. Ring 41 is sized to extend over and move along the length of the rod 101. A fastener 42 provides for securing the ring 41 at the desired axial position on the rod 101.

Figure 8:
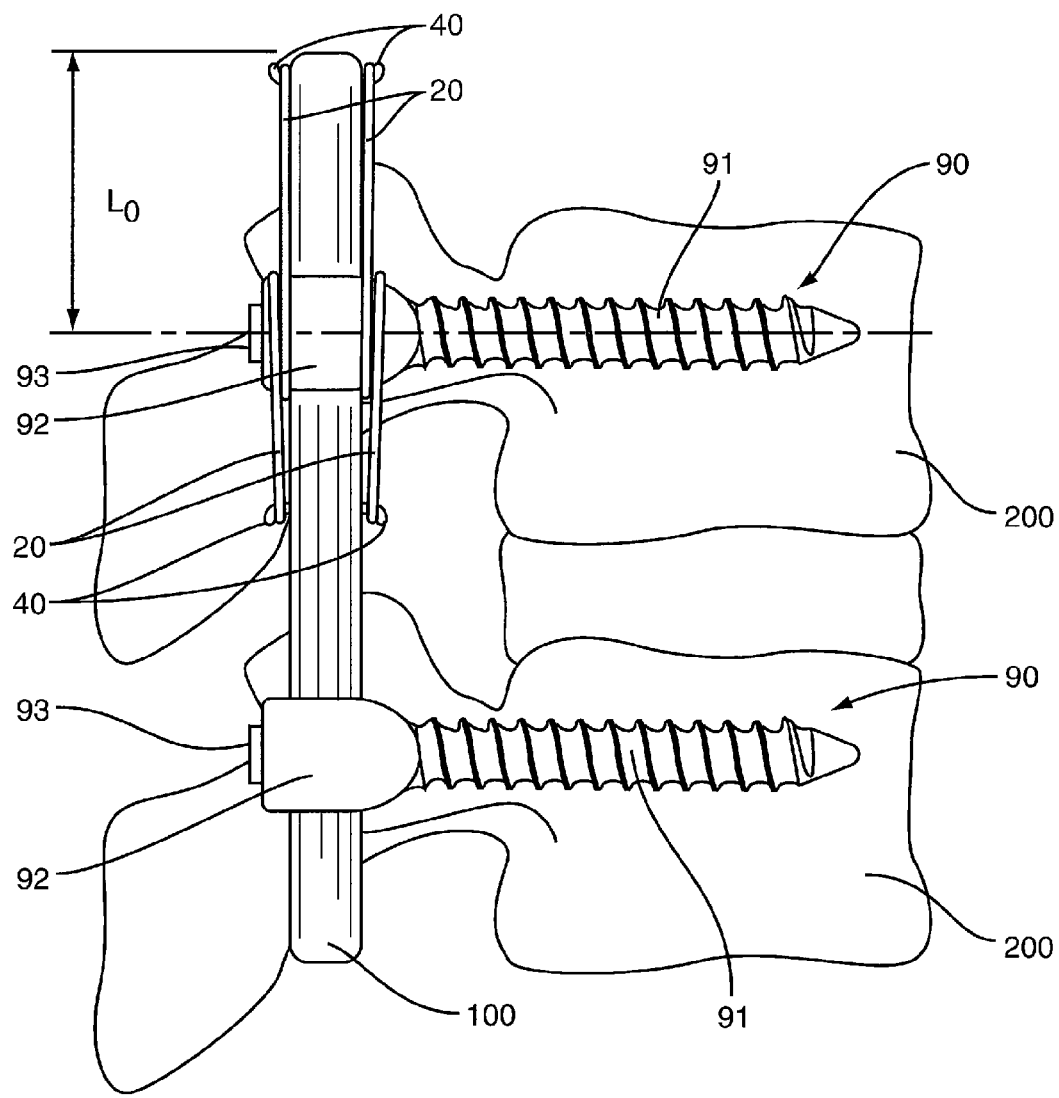
FIG. 8 is a side view illustrating a device according to one embodiment.

In another embodiment as illustrated in FIG. 4, the elastic members 20 connect directly to the saddle 92. The connection may include adhesives, mechanical fasteners 42, soldering, brazing, etc. FIG. 8 illustrates another embodiment with the elastic members 20 shaped as bands that extend around the saddle 92 and arms 40.

In one embodiment, the elastic members 20 provide for asymmetrical movement of the vertebral members 200. The members 20 apply a force to the rod 100 to control the relative movement between the anchor 90 and the rod 100. The force increases relative to the amount of vertebral movement. Elastic members 20 may further include a maximum amount of stretch that sets the amount of vertebral movement.

Figure 1B:
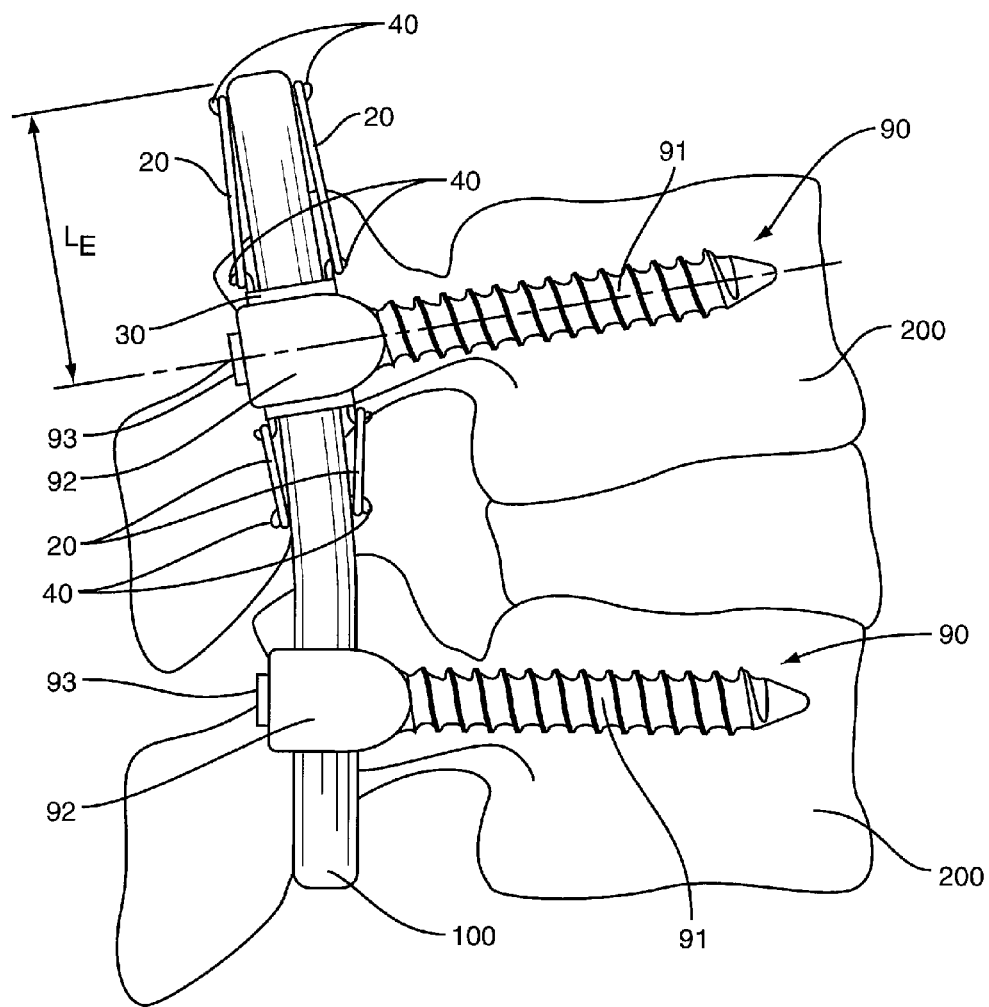
Figure 1C:
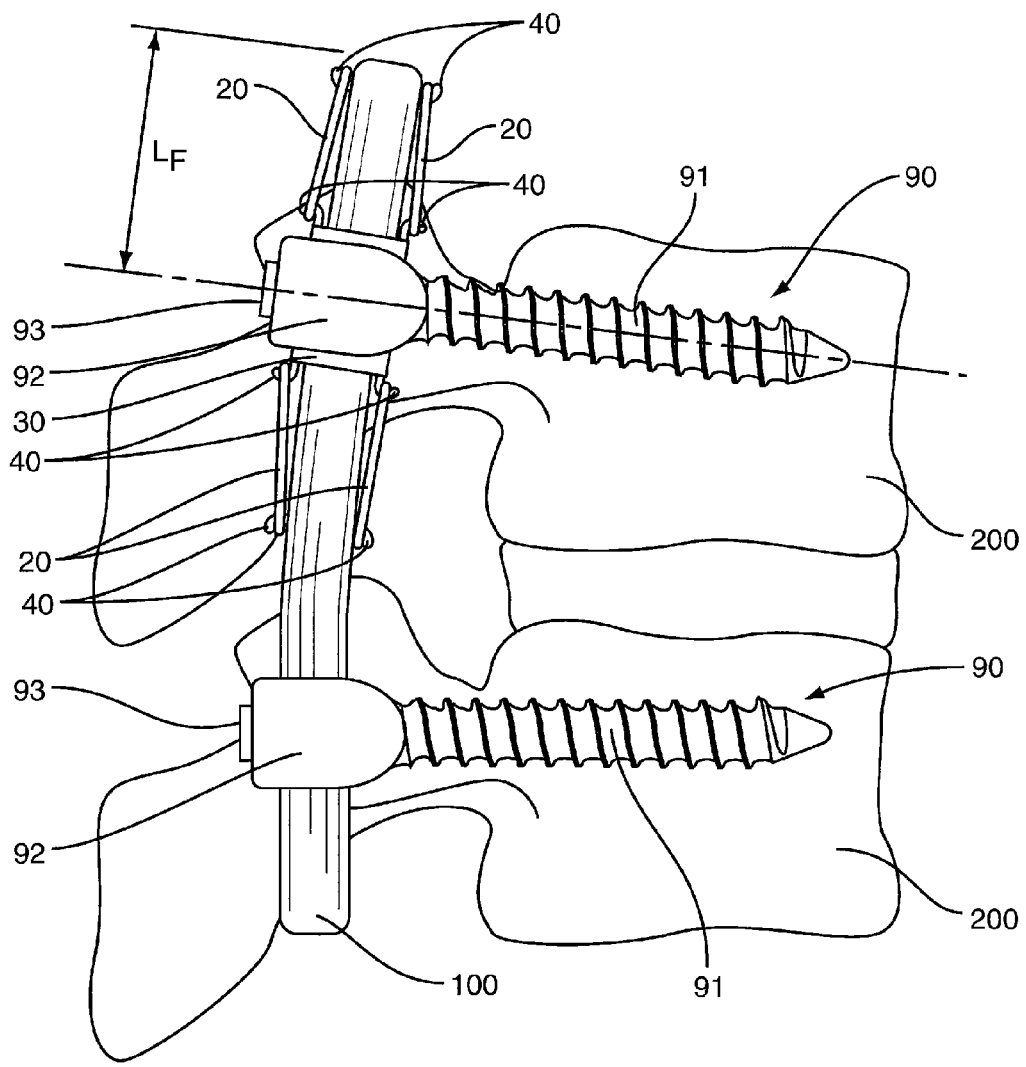

FIGS. 1A-C illustrates one embodiment that supports the vertebral members 200 during extension and flexion. In this embodiment, rod 100 is fixedly attached to a first inferior anchor 90 (i.e., the lower anchor as illustrated in the Figures) and movably attached to the second superior anchor 90. The fastener 93 within the inferior anchor 90 maintains the rod 100 and prevents movement relative to the lower anchor 90. A sleeve 30 that fits around the rod 100 is seated within the saddle 92 of the superior anchor 90. The sleeve 30 may be fixedly maintained within the saddle 92 by the fastener 93. The inner diameter of the sleeve 30 is greater than the outer diameter Y of the rod 100 to allow the rod 100 to slide during movement of the vertebral members 200.

FIG. 1A illustrates an embodiment with the vertebral members 200 in a neutral position. This may include when the patient is standing erect or in a prone position. Elastic members 20 extend between the sleeve 30 and the rod 100. In this embodiment, the two inferior members 20 are taut with the superior members 20 stretched and in an elongated orientation. In this neutral position, a distance $L_O$ extends between a superior end of the rod 100 and the middle of the superior saddle 92.

FIG. 1B illustrates the vertebral members 200 in extension that causes relative movement between the sleeve 30 and rod 100. In this embodiment, the sleeve 30 moves in an inferior direction relative to the rod 100. As illustrated by comparing FIG. 1B with FIG. 1A, the length $L_E$ between the superior end of the rod 100 and the middle of the superior saddle 92 is greater than the distance $L_O$ in the neutral orientation. This relative movement stretches the superior elastic members 20. As the stretching increases, the amount of force applied by the elastic members 20 increases. The increased force reduces the extent of movement of the sleeve 30 and hence the extension of the vertebral members 200. The sliding movement also causes the inferior elastic members 20 to become flaccid.

FIG. 1C illustrates the vertebral members 200 in flexion. This movement causes relative movement of the sleeve 30 in a superior direction. As illustrated by comparing FIG. 1C with FIG. 1A, the distance between the superior end of the rod 100 and the middle of the superior saddle 92 defined as $L_F$ is less than the distance $L_O$ in the neutral orientation. The movement stretches the inferior elastic members 20. As the stretching increases, the amount of force applied by the elastic members 20 increases. The increased force reduces the extent of relative movement of the sleeve 30 and hence the flexion of the vertebral members 200.

In one embodiment, as the amount of extension and flexion from the neutral position increases, the elastic members 20 apply an increasing amount of force to return the rod 100 towards the neutral orientation. Elastic members 20 may include a maximum stretch length that establishes the maximum amount of movement of the vertebral members 200.

FIG. 1A illustrates the elastic members 20 in a first state when the vertebral members 200 are in a neutral orientation. Other embodiments may include the elastic members 20 in other states. In one embodiment, each of the elastic members 20 is substantially flaccid in the neutral orientation.

In one embodiment, the rod 100 supports vertebral members in the cervical region. The range of extension motion is between about 0°-20° and the range of flexion is between about 0°-30°. In one embodiment supporting the lumbar region, the range of extension motion is between about 0°-15° and the range of flexion is between about 0°-25°. Therefore, the elastic members 20 are positioned and structured to cause asymmetrical vertebral motion with additional range of motion in flexion than in extension. In one embodiment, these ranges may be changed for the specific patient and context of use.

Figure 7A:
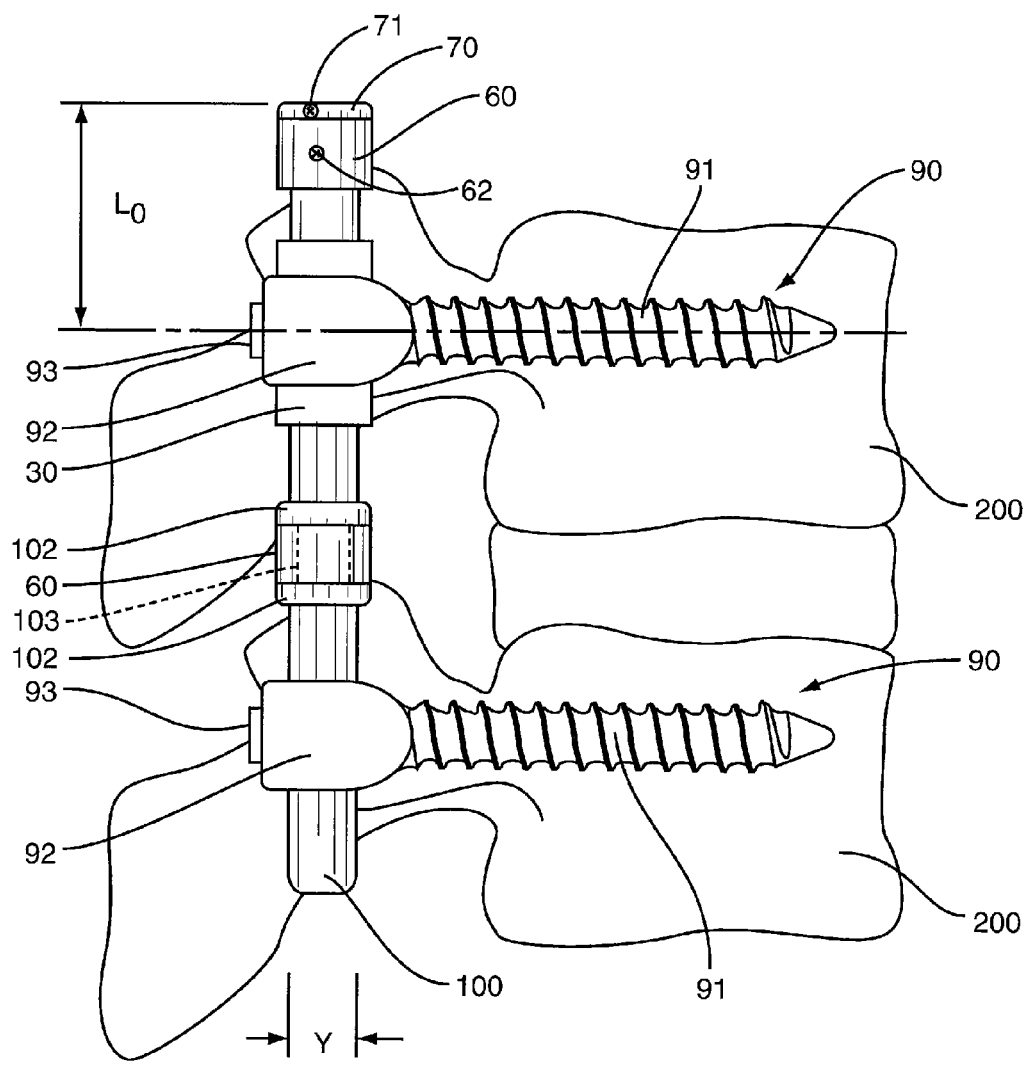
FIGS. 7A-C are side views illustrating a device according to one embodiment.

FIG. 7A illustrates another embodiment for asymmetrical vertebral motion. This embodiment features one or more anchors 90 that attach the rod 100 to the vertebral members 200. A sleeve 30 fits within the superior saddle 92 to allow relative movement between the anchor 90 and the rod 100. Stop members are attached to the rod 100 to control the maximum extent of relative movement of the sleeve 30. In the embodiment of FIG. 7A, stop members include a locking member 70 and flange 102 that are fixedly positioned on the rod 100. These stop members include enlarged widths that are greater than the inner diameter of the sleeve 30 thus preventing the sleeve 30 from moving beyond the member. The stop members may be integrally formed with the rod 100, or may be attached to the rod 100 such as by fasteners 71.

Bumpers 60 are positioned along the rod 100 to control the relative movement of the sleeve 30. In one embodiment, bumpers 60 are constructed of a deformable material with a stiffness that cushions the movement of the sleeve 30 as it approaches and/or contacts the stop members. The bumpers 60 may be positioned along the rod 100 to directly contact the sleeve 30, or to contact the stop members. The bumpers 60 may be permanently or removably attached to the rod 100. In one embodiment as illustrated in FIG. 7A, the superior bumper 60 includes a fastener 62 that attaches the bumper 60 to the rod 100. In another embodiment, the bumper 60 is integrally connected with the locking member 70, such as by being over-molded onto the locking member 70. Bumpers 60 may further be attached to the rod 100 and movable along the length.

Bumpers 60 may include a variety of shapes, sizes, and constructions. In one embodiment, bumpers 60 include a cylindrical shape that extends around the rod 100. In one embodiment, bumpers 60 are modular and can be removed from the rod 100 and replaced as necessary. In one embodiment, the modular bumpers 60 may include different lengths and diameters to control the movement of the vertebral members 200. Modular bumpers 60 may further include different stiffnesses depending upon the application. In embodiments including multiple bumpers 60, the bumpers may include the same of different stiffnesses. Bumpers 60 may be constructed from a variety of materials including polycarbonate urethane, silicone, neoprene, latex, polyurethane, butyl, and polyethylene foam.

In the embodiment of FIG. 7A, a first bumper 60 is positioned on an inferior side of the sleeve 30 between flanges 102. In one embodiment, bumper 60 is positioned around a narrowed section 103 of the rod 100 that extends between the flanges 102. A second bumper 60 is positioned on a superior side of the sleeve 30.

Figure 7B:
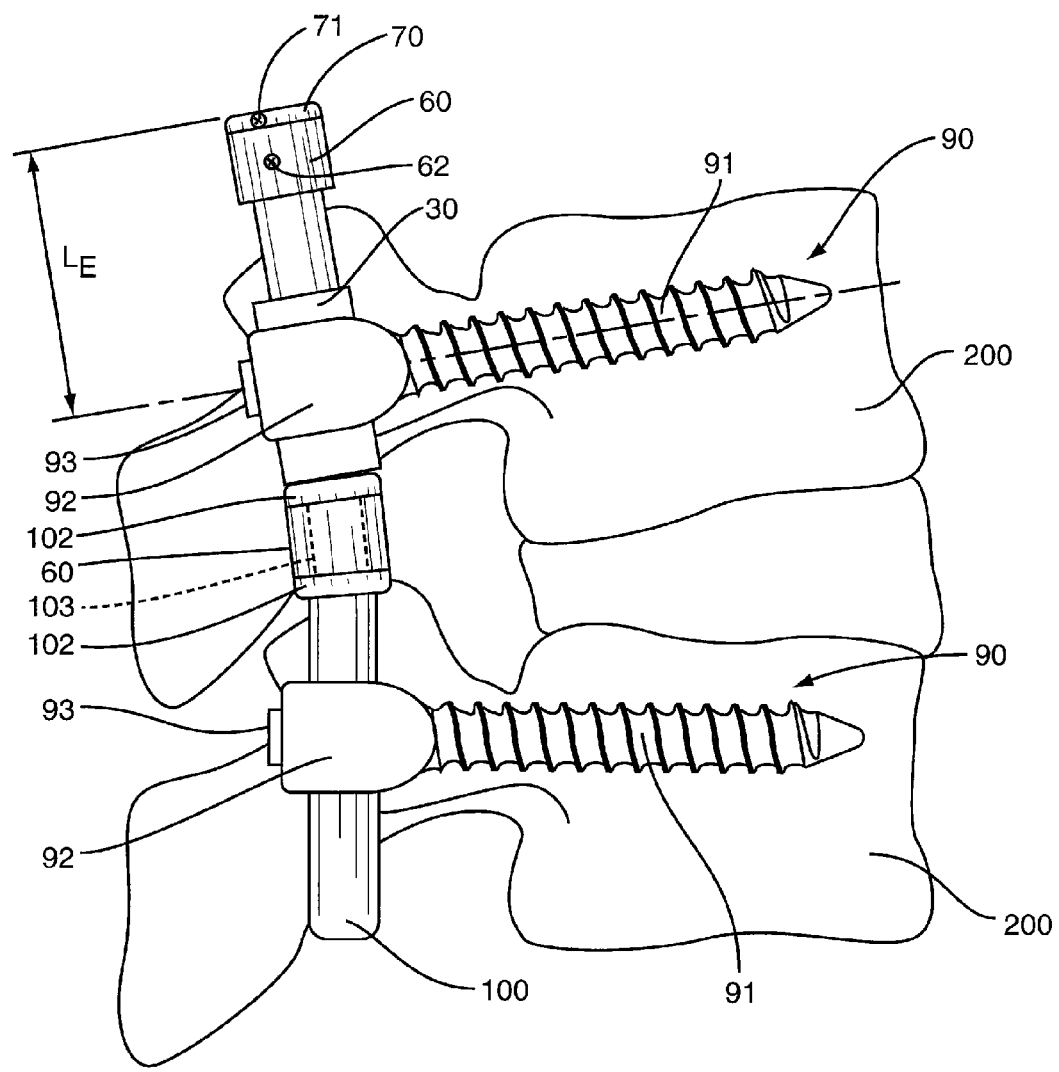
Figure 7C:
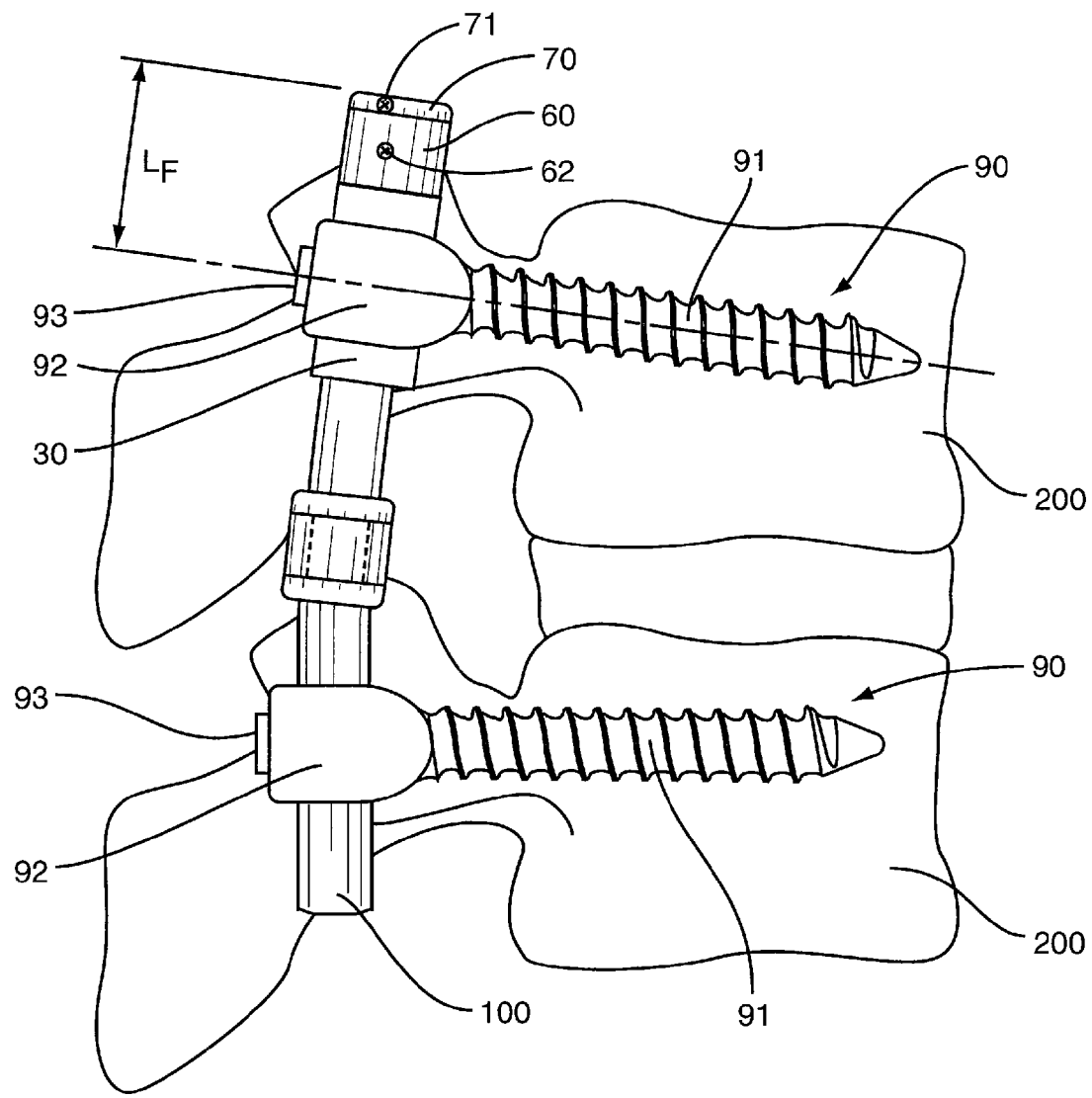

FIGS. 7A-7C illustrates one embodiment of a device to provide asymmetrical movement to the vertebral members 200. In a neutral position as illustrated in FIG. 7A, the vertebral members 200 are aligned such as when the patient is standing upright or in a prone position. In this embodiment, the sleeve 30 is positioned between and spaced away from the bumpers 60. A distance $L_O$ is defined between the center of the superior saddle 92 and the superior end of the rod 100.

FIG. 7B illustrates one embodiment of the vertebral members 200 in extension. This movement causes the position of the sleeve 30 to move in an inferior direction relative to the rod 100. The distance $L_E$ between the center of the superior saddle 92 and the superior end of the rod 100 is enlarged and greater than the neutral position $L_O$. The movement causes the sleeve 30 to contact the superior flange 102 that limits the extent of movement. In one embodiment, the relative movement of the sleeve 30 may cause the inferior bumper 60 to be compressed. The movement may also cause the rod 100 to bend causing the inferior bumper 60 to be deformed with the posterior side being in compression, and may cause the anterior side to be in tension.

FIG. 7C illustrates the vertebral members 200 in flexion. This movement causes the sleeve 30 to move in a superior direction relative to the rod 100. The amount of movement is limited by the locking member 70. The sleeve 30 may contact the bumper 60 causing it become deformed as it is compressed between the sleeve 30 and the locking member 70. The distance $L_F$ between the center of the superior saddle 92 and the superior end of the rod 100 is now smaller than in the neutral position. The vertebral movement may also cause the rod 100 to pivot or bend. In one embodiment, the inferior bumper 60 is deformed by the movement of the rod 100. In one embodiment as illustrated in FIG. 7C, the anterior side of the inferior bumper 60 is compressed by the movement of the rod 100, and the posterior side may be in tension.

In one embodiment of the device illustrated in FIGS. 7A-7C, the rod 100 supports vertebral members in the cervical region and provides for extension of between about 0°-20° and flexion of between about 0°-30°. In one embodiment supporting the lumbar region, the range of extension motion is between about 0°-15° and the range of flexion is between about 0°-25°.

FIG. 7A illustrates an embodiment with the sleeve 30 in a space formed between the superior bumper 60 and the flange 102. In other embodiments, bumper 60 includes a longer length and is in contact with the sleeve 30 when in the neutral position. Further, a second bumper is positioned on a superior side of flange 102 and contacts the inferior side of the sleeve 30. Movement of the vertebral members 200 causes deformation of the bumpers 60.

Figure 10:
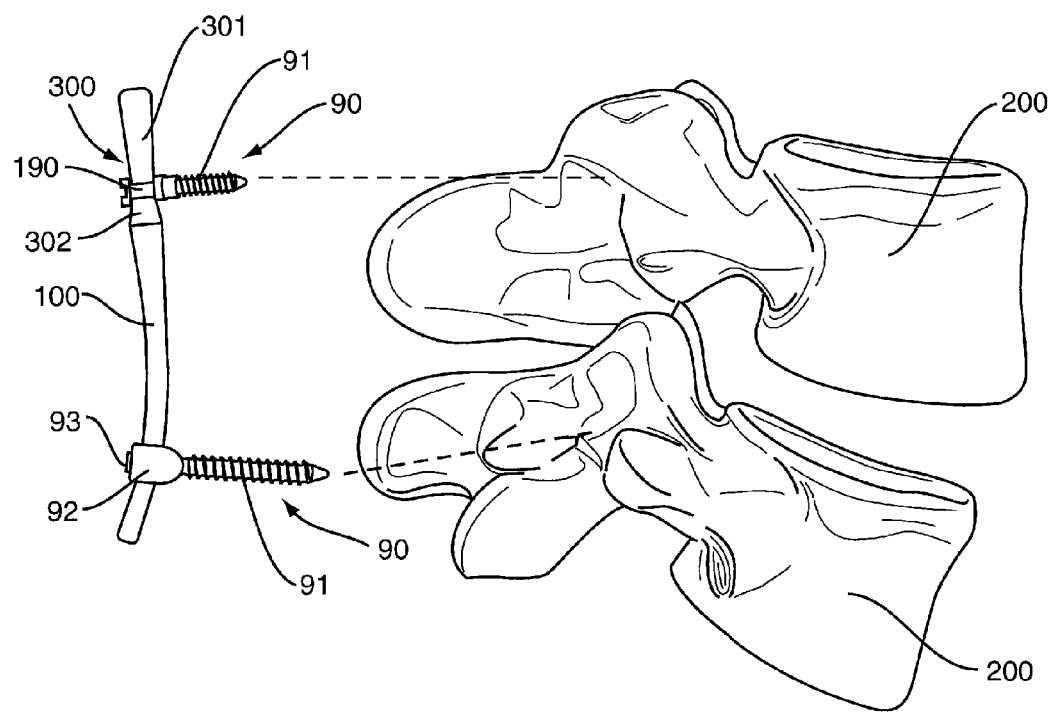
FIG. 10 is a side view illustrating a device according to one embodiment.

FIG. 10 illustrates another embodiment of the rod 100 with a bi-conical section 300 comprising a first tapered section 301 and a second tapered section 302. The inferior anchor 90 is fixedly connected to the rod 100 through a saddle 92 and fastener 93 in a same manner as previously described for the other embodiments. The superior anchor 90 is movably positioned relative to the rod 100.

Figure 11:
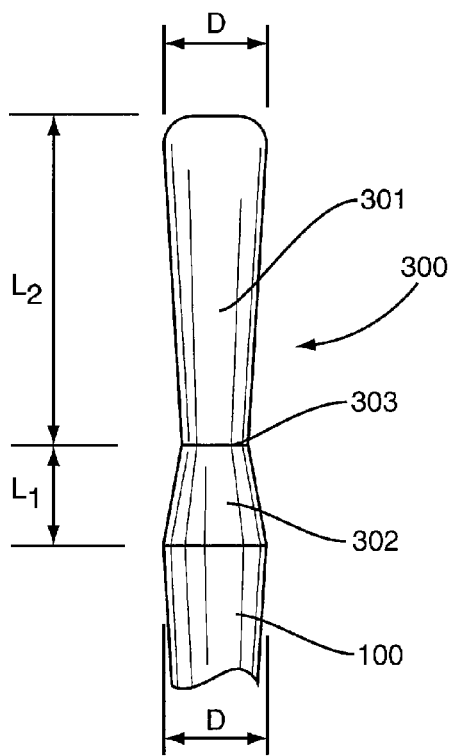
FIG. 11 is a side view illustrating a bi-conical section of a rod according to one embodiment.

FIG. 11 illustrates a section of the rod 100 including the bi-conical section 300. This section 300 includes the first tapered section 301 with a length L2 that tapers outward from a narrow central section 303. The second tapered section 302 includes a length L1 and tapers outward in an opposite direction from the central section 303. Each section 301, 302 terminates at a point along the rod 100 with a diameter D. In this embodiment, the first tapered section 301 is positioned at an end of the rod 100, although other embodiments may feature the bi-conical section 300 at various positions along the rod 100.

Figure 12:
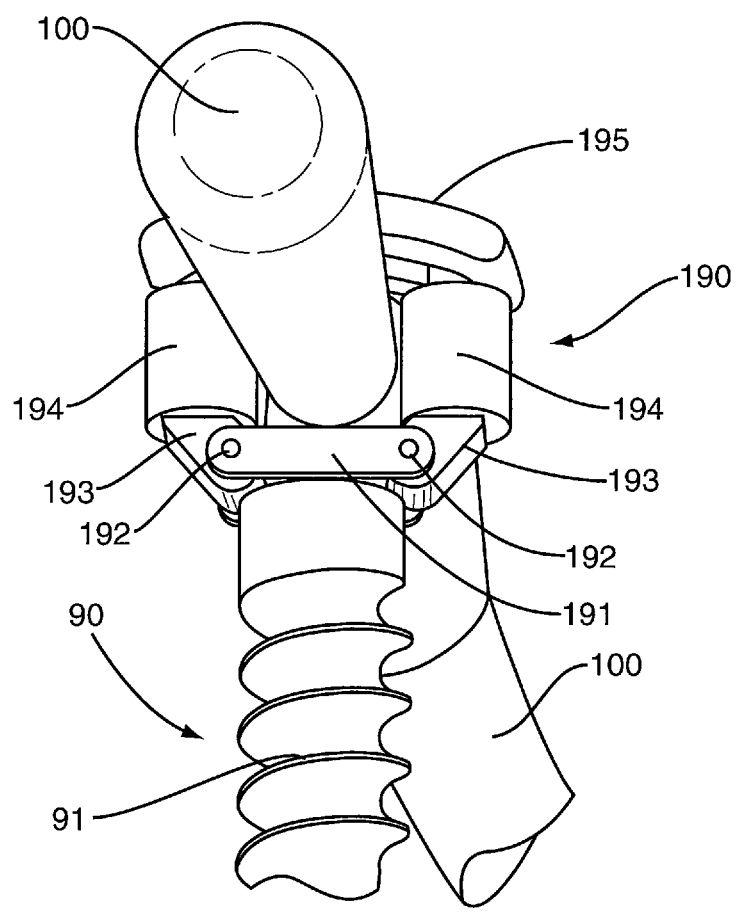
FIG. 12 is a perspective view illustrating an anchor according to one embodiment.

FIG. 12 illustrates the superior anchor 90 that includes a shaft 91 and a head 190. Head 190 includes a base 191 with opposing arms 193 that extend outward from hinges 192. Roller bearings 194 may be mounted on each of the arms 193. The arms 193 may be spring-biased inwards to maintain the roller bearings 194 in contact with the rod 100 during vertebral movement. The arms 193 are hingedly connected to the base 191 and movable between a first inward position forming a first width between the arms 193, and a second outward position forming a second greater width. The second outward position is less than the diameter D to maintain the head 190 in contact with the bi-conical section 300 and control an extent of movement. A top 195 extends between the arms 193 and entraps the rod 100.

Figure 13A:
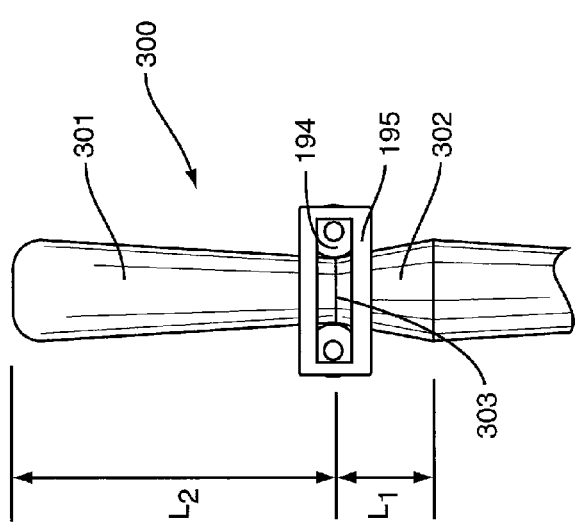
FIGS. 13A-C are side views illustrating a device according to one embodiment.
Figure 13B:
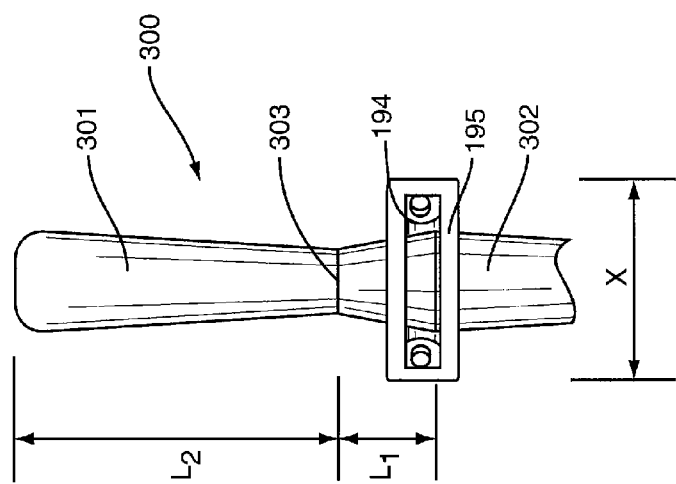
Figure 13C:
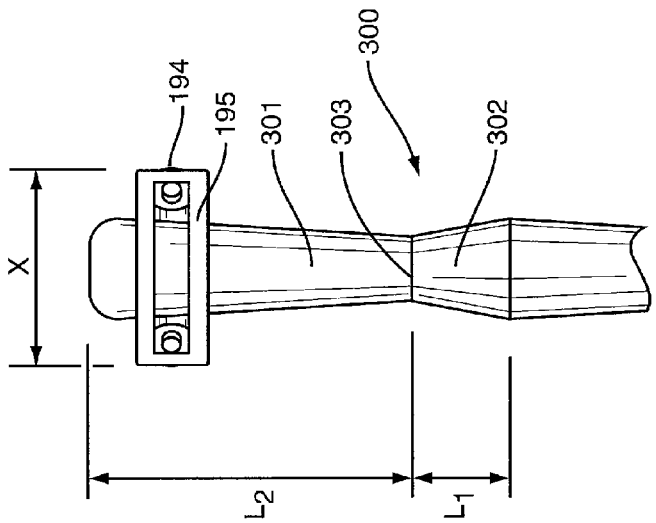

FIG. 13A illustrates the rod 100 when the vertebral members 200 are in a neutral position. The central section 303 is aligned within the head 190 with the rollers bearings 194 aligned with the central section 303. FIG. 13B illustrates the position with the vertebral members 200 in extension. The relative position of the superior anchor 90 has moved along the rod 100 with the head 190 in contact with the second tapered section 302. The extent of movement along the section 302 is controlled because the arms 193 do not extend beyond a width greater than the diameter D of the rod 100 outside the bi-conical section 300. FIG. 13C illustrates the position with the vertebral members 200 in flexion. The relative position of the superior anchor 90 has moved with the head 190 now along the first tapered section 301. Again, the extent of movement is controlled because the arms 193 do not move to a width greater than the diameter D.

In one embodiment, the arms 193 apply a compressive force to the sections 301, 302 during vertebral movement. The amount of compressive force is predicated on the width of the section 301, 302. A smaller width, such as in proximity to the central section 303, causes a smaller compressive force than a larger width towards the outer edges of the sections 301, 302. Therefore, the amount of force applied increases with the increased extent of vertebral movement in each of the directions.

Figure 14A:
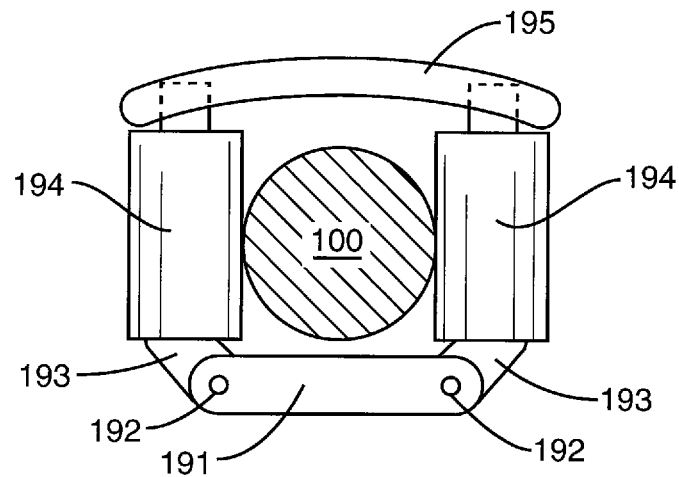
FIGS. 14A-14B are cross section views of the rod positioned within an anchor according to one embodiment.
Figure 14B:
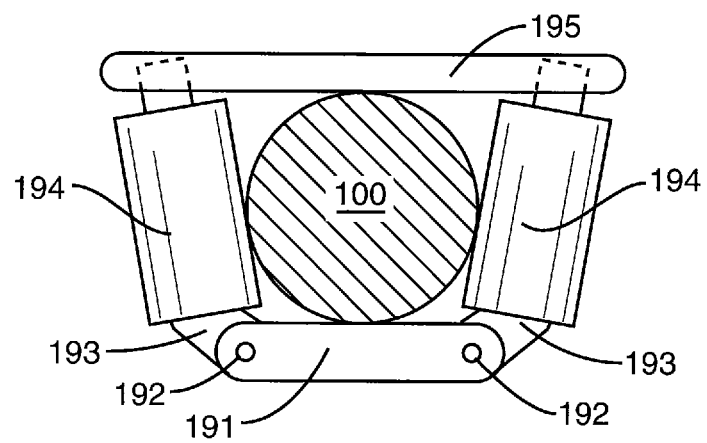

FIGS. 14A and 14B illustrate a side view of the head 190 and rod 100. FIG. 14A illustrates the head 190 in a first orientation, such as when the vertebral members 200 are in a neutral position. The arms 193 are positioned with the roller bearings 194 in contact with the rod 100. The top 195 may include a bowed configuration and extend between an upper section of the arms 193. FIG. 14B illustrates the head 190 in a second orientation, such as when the vertebral members 200 are in flexion. The enlarged tapered section 301 is aligned with the head 190 causing the arms 193 to move outward but maintain the roller bearings 194 in contact with the rod 100. The top 195 has changed to a straightened configuration due to the movement of the arms 193. In one embodiment, the extent of arm 193 movement is limited by the top 195.

The lengths and widths of the tapered sections 301, 302 may vary depending upon the context of use. In the embodiment illustrated, the central section 303 has substantially no length as it comprises the intersection of the sections 301, 302. In other embodiments, the central section 303 may include a length such that vertebral movement is not hindered until the head 190 begins to move along one of the sections 301, 302.

Figure 9:
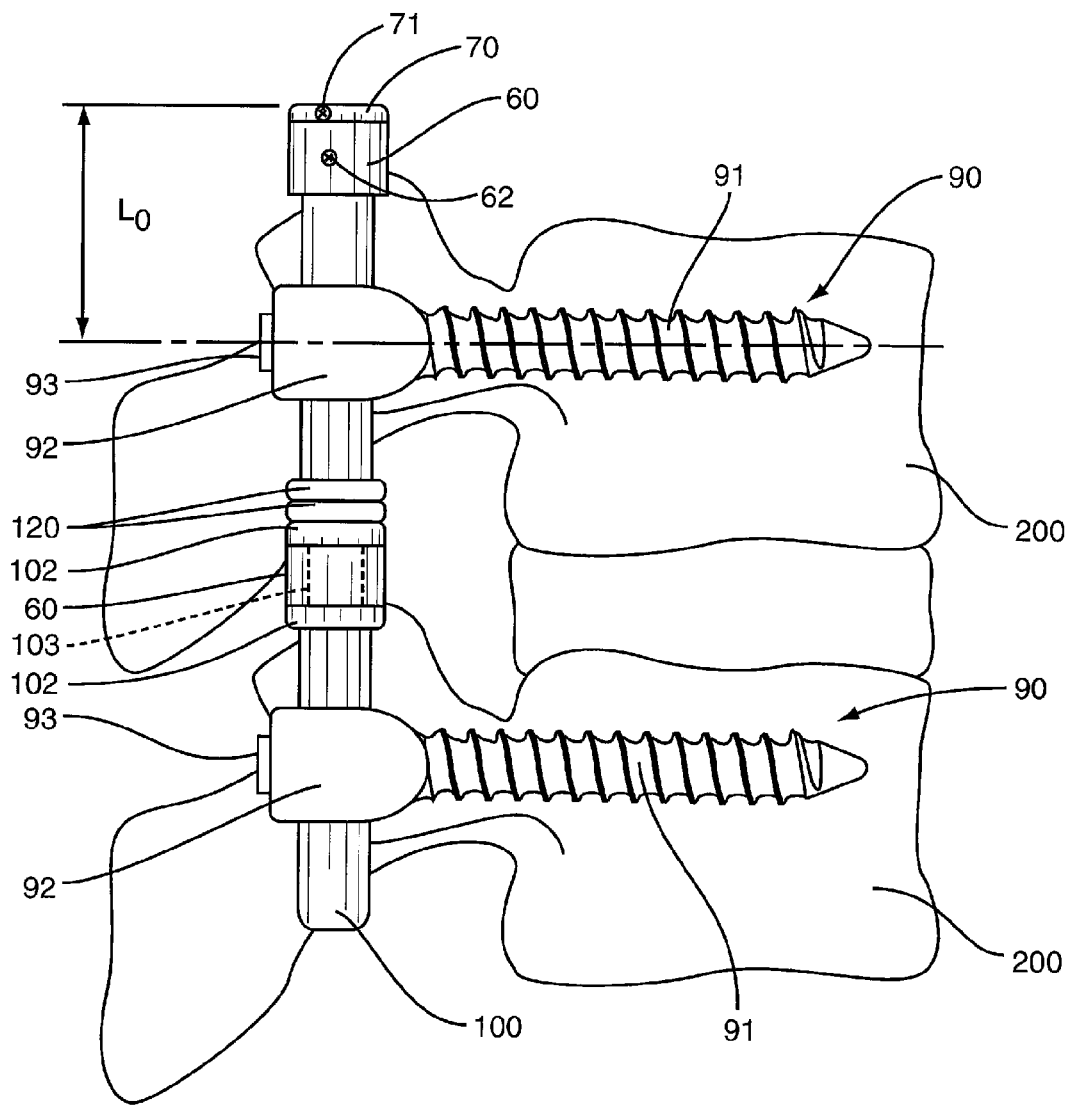
FIG. 9 is a side view illustrating a device according to one embodiment.

In one embodiment as illustrated in FIGS. 1A-C and 7A-C, the rod 100 slides within a sleeve 30 positioned within the saddle 92. In another embodiment as illustrated in FIGS. 8 and 9, the rod 100 slides within the saddle 92 during vertebral movement. The saddle 92 is sized to allow for sliding movement of the rod 100. In one embodiment, fastener 93 closes the saddle 92 and prevents escape of the rod 100.

Stops 120 as illustrated in FIG. 9 may be positioned along the rod 100 to control the extent of movement. The stops 120 are positioned to adjust the rod length that is available for movement. In one embodiment, stops 120 are C-shaped members that may be deformed to attach to the rod 100 and then return to their original shape to maintain attachment. In the embodiment of FIG. 9, the saddle 92 contacts the stops 120 during extension to limit the amount of vertebral movement. Without the stops, the amount of movement would be larger and controlled by contact of the saddle 92 with the flange 102. Stops 120 may be constructed of a variety of materials including polyethylene, polyetheretherketone, polycarbonate urethane, titanium, cobalt chrome, silicone, neoprene, latex, polyurethane, butyl, and polyethylene foam.

The various components may be changed and/or replaced after the device has been inserted in the patient. By way of example, the elastic members 20 may be replaced with ones having different constructions (e.g., sizes, stiffnesses) to adjust the vertebral movement as necessary. Further, stops 120 may be placed along the rod 100, and the position of the locking member 70 may be adjusted. These revisions procedures may be conducted in a minimally-invasive manner.

The embodiments illustrated in FIGS. 1A-C, 7A-C, and 10 illustrates a rod 100 that spans across two vertebral members 200. In another embodiment, rod 100 includes a greater length to span across more than two vertebral members 200. These embodiments further illustrate two anchors 90 attaching the rod 100 to the vertebral members 200. In other embodiments, more than two anchors 90 attach the rod 100 to two or more vertebral members 200.

In the embodiments illustrated in FIGS. 1A-1C, 7A-7C, 10, and 13A-13C, the inferior anchor 90 is fixedly attached to the rod 100 with relative movement occurring at the superior anchor 90. In another embodiment, the superior anchor 90 may be fixedly attached with relative movement occurring between the inferior anchor 90 and the rod 100. In one embodiment, the rod 100 is initially curved.

In one embodiment, the rod 100 is constructed of a flexible material that bends during movement of the vertebral members 200. In one embodiment, the rod 100 is constructed of a material that does not bend during the movement.

The term "distal" is generally defined as in the direction of the patient, or away from a user of a device. Conversely, "proximal" generally means away from the patient, or toward the user. Spatially relative terms such as "under", "below", "lower", "over", "upper", and the like, are used for ease of description to explain the positioning of one element relative to a second element. These terms are intended to encompass different orientations of the device in addition to different orientations than those depicted in the figures. Further, terms such as "first", "second", and the like, are also used to describe various elements, regions, sections, etc and are also not intended to be limiting. Like terms refer to like elements throughout the description.

As used herein, the terms "having", "containing", "including", "comprising" and the like are open ended terms that indicate the presence of stated elements or features, but do not preclude additional elements or features. The articles "a", "an" and "the" are intended to include the plural as well as the singular, unless the context clearly indicates otherwise.

The present invention may be carried out in other specific ways than those herein set forth without departing from the scope and essential characteristics of the invention. The present embodiments are, therefore, to be considered in all respects as illustrative and not restrictive, and all changes coming within the meaning and equivalency range of the appended claims are intended to be embraced therein.

What is claimed is:

1. A device to support first and second vertebral members comprising:
   a first anchor attached to the first vertebral member;
   a second anchor attached to the second vertebral member;
   an elongated member including a first longitudinal section mated to the first anchor and a second longitudinal section mated to the second anchor for sliding motion relative thereto;
   a first element connected to the elongated member on a first side of the second anchor between the first and second anchors;
   a second element connected to the elongated member at a second side of the second anchor; and
   the first and second elements each being tension members that are operative to apply tension forces in opposing directions that impede relative movement of the first and second vertebral members via sliding motion between the elongated member and the second anchor, the first element applying a first tension force in a first direction during movement of the elongated member relative to the second anchor in a first direction, and the second element applying a second tension force in a second opposing direction during movement of the elongated member relative to the second anchor in a second direction.

2. The device of claim 1, further comprising a cylindrical sleeve positioned within the second anchor and extending around the elongated member, an inner diameter of the sleeve being larger than an outer diameter of the elongated member to allow the elongated member to slide within the sleeve.

3. The device of claim 2, wherein the first and second elements are connected to the sleeve.

4. The device of claim 1, wherein the first and second elements are connected to the second anchor.

5. The device of claim 1, wherein the first and second elements are constructed of an elastic material.

6. The device of claim 1, wherein the elongated member is constructed of a flexible material that bends during movement of the first and second vertebral members.

7. The device of claim 1, further comprising a stop member removably mounted to the rod at a point between one of the first and second elements and the second anchor.

8. A device to support first and second vertebral members comprising:
   a first anchor attached to the first vertebral member;
   a second anchor attached to the second vertebral member;
   an elongated rod including a first longitudinal section fixedly mated to the first anchor, a second longitudinal section defined between the first and second anchors, and a third longitudinal section defined between the second anchor and an end of the rod;
   a first element connected to the second longitudinal section to impede movement of the elongated rod relative to the second anchor in a first amount in a first direction from a neutral position;
   a second element associated with the third longitudinal section to impede movement of the elongated rod relative to a second anchor in a second direction away from the neutral position, the second direction being opposite from the first direction;
   the first element configured to apply a first tension force to the elongated rod during movement of the elongated rod in the first direction, and the second element configured to apply a second tension force to the elongated rod during movement of the elongated rod in the second direction;
   wherein the elongated rod is slidably supported by the second anchor.

9. The device of claim 8, wherein a length of the second longitudinal section increases during movement of the vertebral members in the first direction from the neutral position.

10. The device of claim 8, wherein a length of the second longitudinal section decreases during movement of the vertebral members in the second direction from the neutral position.

11. The device of claim 8, wherein the first and second anchors each comprise saddles for receiving the elongated rod.

12. The device of claim 8, wherein the elongated rod is constructed of a flexible material that bends during movement of the vertebral members in the first and second directions.

13. The device of claim 8, wherein the elongated rod includes a first arm positioned within the second longitudinal section and a second arm positioned within the third longitudinal section, each of the arms extending outward from an axis of the elongated rod to attach to one of the first and second elements.

14. The device of claim 8, wherein the second anchor further comprises a sleeve with an opening to receive the elongated rod, the opening being larger than the elongated rod for the elongated rod to slide within the sleeve.

15. The device of claim 8, wherein the first and second elements are elastic bands with each of the bands positioned on a single lateral side of the rod.

16. A device to support first and second vertebral members comprising:
   a first anchor attached to the first vertebral member;
   a second anchor attached to the second vertebral member;
   an elongated member fixedly mated to the first anchor and slidingly mated to the second anchor for sliding motion relative thereto in first and second opposing directions, the elongated member including a longitudinal axis;
   a first elastic element extending between the second anchor and the elongated member at a first side of the second anchor;
   a second elastic element extending between the second anchor and the elongated member at a second side of the second anchor; and
   the first and second elastic elements being operative to impede relative movement of the first and second vertebral members via sliding motion between the elongated member and the second anchor, the first elastic band configured to be in tension and apply a first force on the elongated member during sliding movement of the elongated member in the first direction and the second elastic band configured to be in tension and apply a second force on the elongated member during sliding movement of the elongated member in the second direction;

the first elastic band configured to prevent affecting the second force during sliding movement of the elongated member in the second direction, and the second elastic band configured to prevent affecting the first force during sliding movement of the elongated member in the first direction;

the first and second elastic bands each being continuous and including an open interior section;

wherein a plane contains the longitudinal axis of the elongated member and the first elastic band is positioned entirely on one side of the plane.

17. The device of claim 16, wherein the first elastic element includes a first stiffness and the second elastic element includes a second, different stiffness.

18. The device of claim 16, wherein the second anchor further comprises a sleeve sized to extend around the elongated member, the first and second elastic elements being connected to the sleeve.

19. The device of claim 18, wherein the sleeve comprises an inner layer that contacts the elongated member and an outer layer that contacts the second anchor, the inner and outer layers being constructed of different materials.

20. The device of claim 17, further comprising a first arm that extends outward from the elongated member on a first side of the second anchor and a second arm that extends outward from the elongated member on a second side of the second anchor, the first arm sized to connect with the first elastic element and the second arm sized to connect with the second elastic element.

21. A device to support first and second vertebral members comprising:

a first anchor attached to the first vertebral member;
a second anchor attached to the second vertebral member;
an elongated rod including a first longitudinal section fixedly mated to the first anchor, a second longitudinal section defined between the first and second anchors, and a third longitudinal section defined between the second anchor and an end of the rod;
a first elastic member operatively connected to the second longitudinal section and configured to be placed in tension and apply a first tension force to the elongated rod during movement of the elongated rod relative to the second anchor in a first direction during a first type of movement of the vertebral members;
a second elastic member operatively connected to the third longitudinal section and configured to be placed in tension and apply a second tension force to the elongated rod during movement of the elongated rod relative to the second anchor in an opposite second direction during a second type of movement of the vertebral members;
wherein the elongated rod is slidably supported by the second anchor.

22. The device of claim 21, wherein the elongated rod is constructed of a flexible material that bends during movement of the vertebral members.

* * * * *